(12) United States Patent
Iwamoto et al.

(10) Patent No.: US 6,756,358 B2
(45) Date of Patent: Jun. 29, 2004

(54) THERAPEUTIC AGENT FOR CARTILAGINOUS DISEASES

(75) Inventors: Masahiro Iwamoto, Minoo (JP); Sumihare Noji, Tokushima (JP); Toshikazu Nakamura, Takatsuki (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/921,874

(22) Filed: Aug. 6, 2001

(65) Prior Publication Data

US 2002/0009432 A1 Jan. 24, 2002

Related U.S. Application Data

(63) Continuation of application No. 08/793,121, filed as application No. PCT/JP95/00121 on Jan. 30, 1995, now abandoned.

(30) Foreign Application Priority Data

Aug. 19, 1994 (JP) .............................................. 6-218164

(51) Int. Cl.[7] .............................................. A61K 38/00
(52) U.S. Cl. ............................. 514/12; 514/2; 530/399
(58) Field of Search ........................ 514/2, 12; 530/399

(56) References Cited

U.S. PATENT DOCUMENTS 5,565,558 A * 10/1996 McCully ..................... 536/26.4
5,723,331 A * 3/1998 Tubo et al. .................. 435/366
6,248,722 B1 * 6/2001 Morishita et al. ............. 514/44

FOREIGN PATENT DOCUMENTS

EP 0517182 12/1992
WO 9530383 11/1995

OTHER PUBLICATIONS

Partial Translation of the 7th Annual Meeting for the Japanese Society of Cartilage Metabolism, p. 32, Abstract, 1994.
*The Role of HGF/SF in Cartilage Formation and Growth*, Connective Tissue, vol. 26, No. 1, p. 49, (1994).

Partial Translation of the 36th Annual Meeting of Japanese Association for Oral Biology, 130–2A 1150 (1994).

Journal of Bone and Mineral Metabolism, Official Publication of the Japanese Society for Bone and Mineral Research, vol. 13, No. 1 (1995).

Kaibori et al., J. Hepatology, 27:381–390 (1997).

Bandara et al., DNA and Cell Bilogy, 11:227–231 (1992).

Gak et al., FEBS Letters, 311:17–21 (1992).

Zioncheck et al., Endocrinology, 134:1879–1887 (1994).

Shima et al., Biochem. Biophys. Res. Commun., 200:808–815 (1994).

Brown, Pathol. Immunopathol. Res., 7:55–61 (1988).

Minor et al., Pathol. Immunopathol. Res., 7:62–67 (1988).

Melvin et al., Pathol. Immunopathol. Res., 7:68–72 (1988).

Eyre, Pathol. Immunopathol. Res., 7:90–94 (1988).

Yukioka et al., J. Rheumatol., 21:2184–2189 (1994).

Rong et al., Cancer Res., 53:5355–5360 (1993).

Wolf et al., Hepatology, 14:488–494 (1991).

* cited by examiner

*Primary Examiner*—Jon P. Weber
(74) *Attorney, Agent, or Firm*—Birch, Stewart, Kolasch & Birch, LLP

(57) ABSTRACT

The present invention relates to a therapeutic agent for cartilaginous diseases, an accelerator for chondrocyte proliferation and an accelerator for proteoglycan production comprising HGF (hepatocyte growth factor) as an active component, and a treatment method for cartilaginous diseases of human or mammals comprising administering an effective amount of HGF. The active component HGF has an effect to promote the proliferation of chondrocytes and to promote the production of proteoglycan. Therefore, the therapeutic agent and accelerator of the present invention are useful for the prevention and treatment of various disorders caused by cartilaginous diseases.

14 Claims, 8 Drawing Sheets

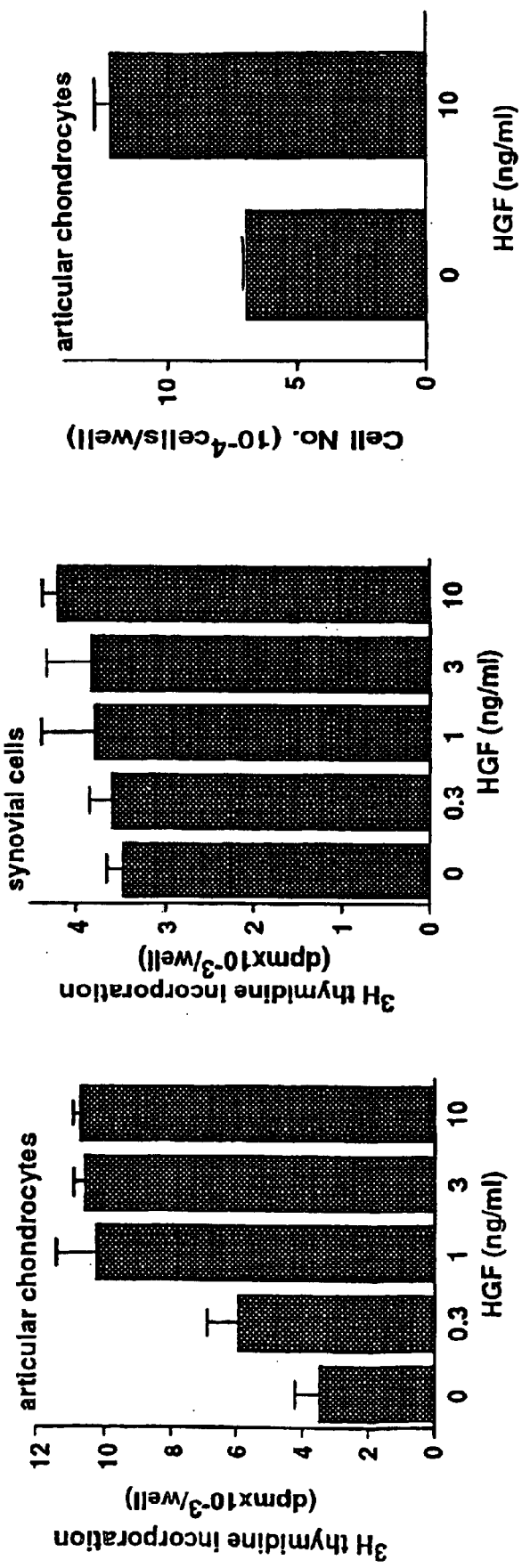

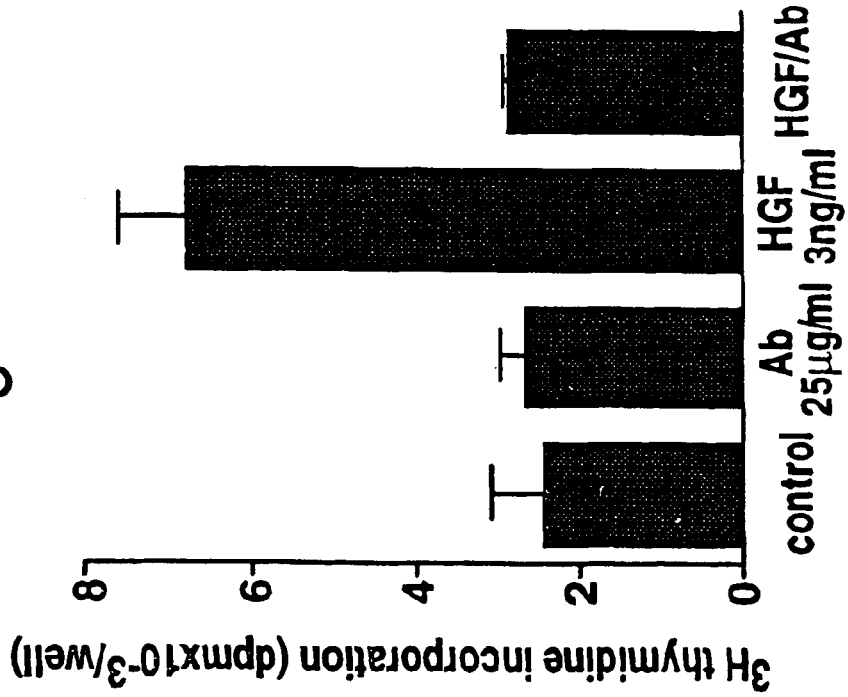
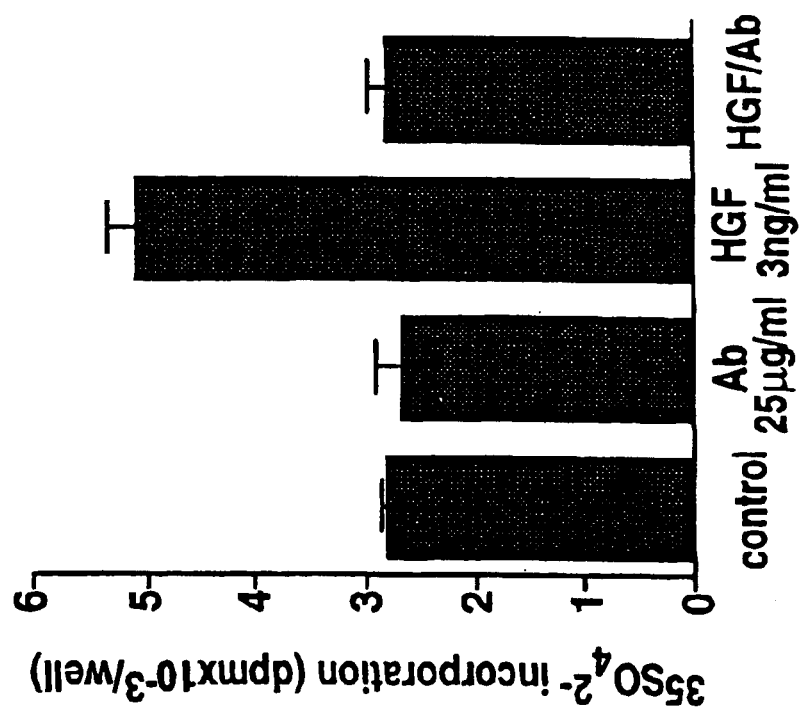
Fig. 7A
Fig. 7B lane

1. Cultured articular chondrocytes (35 cycles)
2. Cultured costal chondrocytes (35 cycles)
3. Marker
4. Articular cartilage tissue (40 cycles)
5. costal cartilage tissue (40 cycles)

THERAPEUTIC AGENT FOR CARTILAGINOUS DISEASES

This application is a continuation of co-pending application Ser. No. 08/793,121, filed on Apr. 21, 1997 now abandoned and for which priority is claimed under 35 U.S.C. §120. application Ser. No. 08/793,121 is the national phase of PCT International Application No. PCT/JP95/00121 filed on Jan. 30, 1995 under 35 U.S.C. § 371. This application also claims priority of Application No. 6-218164 filed in Japan on Aug. 19, 1994 under 35 U.S.C. § 119. The entire contents of each of the above-identified applications are hereby incorporated by reference.

TECHNICAL FIELD

The present invention relates to a medicine useful for the prevention and treatment of cartilaginous diseases. More particularly, the present invention relates to a therapeutic agent for cartilaginous diseases, an accelerator for chondrocyte proliferation and an accelerator for proteoglycan production comprising HGF (Hepatocyte Growth Factor) as an active component.

BACKGROUND ART

Cartilage is a connective tissue composed of chondrocytes and matrices surrounding them, and exists in articulatio, intervertebral disk of spina, costal cartilage, auricle, external acoustic meatus, pubic symphysis, throat tectum and the like. Cartilage is composed of chondrocytes and cartilage matrices produced by the chondrocytes, and the cartilage matrix consists mainly of a fiber component such as a collagen fiber, proteoglycan and water. Cartilage can be classified into hyaline cartilage (costal cartilage, throat cartilage, articular cartilage and the like), elastic cartilage (auricle cartilage and the like) and fibrocartilage (intervertebral disk cartilage, pubic bone cartilage, articular cartilage and the like) depending on the mixing condition of a cartilage matrix. In the aforesaid cartilage matrix, it is said that the collagen fiber concerns the stiffness and strength of cartilage against tension and shear force, proteoglycan concerns the strength of cartilage against compression force, and water manifests a feature as a viscoelastic material for an organism tissue, and for example, in the articular cartilage, 78.6% of the weight of cartilage is occupied by water, 20% is occupied by collagen and 7% is occupied by proteoglycan. The effect of cartilage includes the reduction in abrasion of epiphysis (cartilage between bones), maintenance of elasticity (auricle cartilage and the like), and motion function (rib cartilage, pubic bone cartilage and the like).

As described above, cartilage has an important effect for maintaining the function of an organism, and conventionally, there are known various disorders caused by cartilage diseases, including, for example, chondrodystrophy, osteoarthritis, diastrophic discopathy, failure in restoration and cure of fracture and the like. Particularly, there has been a remarkable increase in the number of the patient suffering from anthropathy because of the arrival an aging society, the increase of injury due to sports and the appearance of occupational diseases represented by keypuncher disease and the like, and there is desired the development of medical care in this field.

Various therapeutic methods have been conventionally tried for the treatment of cartilage diseases. They were not intended for direct solution of causes, but were only nosotropic methods, for example, a method in which disorder such as pain due to the disease is inhibited by administering an antiphlogistic; a method in which the motion of an articulatio is made smooth by injecting a hyaluronic acid preparation into the articulatio, and the like.

As described above, radical therapeutics for articular disorders has not been found, and there are many patients suffering from osteoarthritis, therefore, an effective therapeutic method for articular disorders is eagerly desired.

The present inventors have been studied intensely to solve the above-mentioned problems. As a result, it has been found that HGF promotes the proliferation of a chondrocyte, has an effect to promote the production of proteoglycan, and is effective for the treatment of various disorders caused by cartilaginous diseases, and the present invention has been completed.

The above-described HGF is a protein which was found as a factor to proliferate liver parenchyma cells in vitro (Biochem Biophys Res Commun, 122, 1450, 1984; Proc. Natl. Acad. Sci. USA, 83, 6489, 1986; FEBS Letter, 224, 311, 1987; Nature, 342, 440, 1989; Proc. Natl. Acad. Sci. USA, 87, 3200, 1990). It has become apparent as a result of the recent studies by many researchers including the present inventors that HGF, which was found as a factor to specifically proliferate liver parenchyma cells, manifests various activities such as the cure of tissue injury in vivo, and HGF is expected to be not only a research object but also therapeutic agents applied to human and animals.

It is known that HGF is produced mainly by mesenchymal cells, and it has become clear that so-called paracrine mechanism exists in which HGF is optionally supplied from adjacent cells. However, it is believed that HGF is supplied also by so-called endocrine mechanism since when liver or kidney is injured, the production of HGF is increased also in the organs which are not injured, for example lung and the like.

Regarding the receptor of HGF, it has been identified form the recent studies that c-Met proto-oncogene codes the HGF receptor (Bottaro et al., Science 251, 802–804, 1991; Naldini et al., Oncogene 6, 501–504, 1991).

As described above, though various information are known regarding HGF, the chondrocyte growth accelerating effect and proteoglycan production accelerating effect are novel knowledge which are conventionally not known, and the present invention accomplished based on the knowledge provides a medicine useful for the treatment of various disorders caused by cartilaginous diseases.

DISCLOSURE OF THE INVENTION

The present invention is a therapeutic agent for cartilaginous diseases comprising HGF as an active component.

Further, the present invention relates to an accelerator for chondrocyte proliferation comprising HGF as an active component; an accelerator for proteoglycan production comprising HGF as an active component; and a therapeutic method for cartilaginous diseases of human or mammals comprising administering an effective amount of HGF.

The above-described HGF may be one derived from the tissue or blood component of human or animals, or one produced by gene recombination.

The active component HGF is effective for the treatment and prevention of various disorders caused by cartilaginous diseases, since HGF promotes the growth of chondrocytes and promotes the production of proteoglycan.

BRIEF EXPLANATION OF THE DRAWINGS

In FIG. 1, each A to D is the longitudinal section of a 10.5 days p.c. embryo, each E to H is the longitudinal section of a 11 days p.c. embryo.

In FIG. 2, each A and B is the section of a 12.5 days p.c. embryo, each C to F is the section of a 13 days p.c. embryo, each G to J is the section of a 14 days p.c. embryo. Further, Fe indicates a femur, Fi indicates a fibula, Ta indicates a tarsal bone, and each I to V indicates digit number.

In FIG. 3, each A and B is the horizontal section of the hind limb of a 16 days p.c. embryo, each C and D is the longitudinal section of the thorax of a 13 days p.c. embryo, each E and F is the longitudinal section of the thorax of a 14 days p.c. embryo. Further, Ta indicates a tarsal bone, Ti indicates a tibia and Rib indicates the precartilaginous condensation of rib cartilage.

In FIG. 4, A indicates control (no-HGF-treatment), B indicates HGF-treatment.

FIG. 5 is a drawing showing the effect of HGF on chondrocyte proliferation. In FIG. 5, A indicates the effect on DNA synthesis of articular chondrocytes, B indicates the effect on DNA synthesis of synovial cells, and C indicates the effect on proliferation (cell number) of articular chondrocytes.

FIG. 7 is a drawing showing the effect of HGF on DNA synthesis (FIG. 7A) and proteoglycan production (FIG. 7B) in the presence of an anti-HGF antibody.

THE BEST MODE FOR CARRYING OUT THE INVENTION

Figure 1:
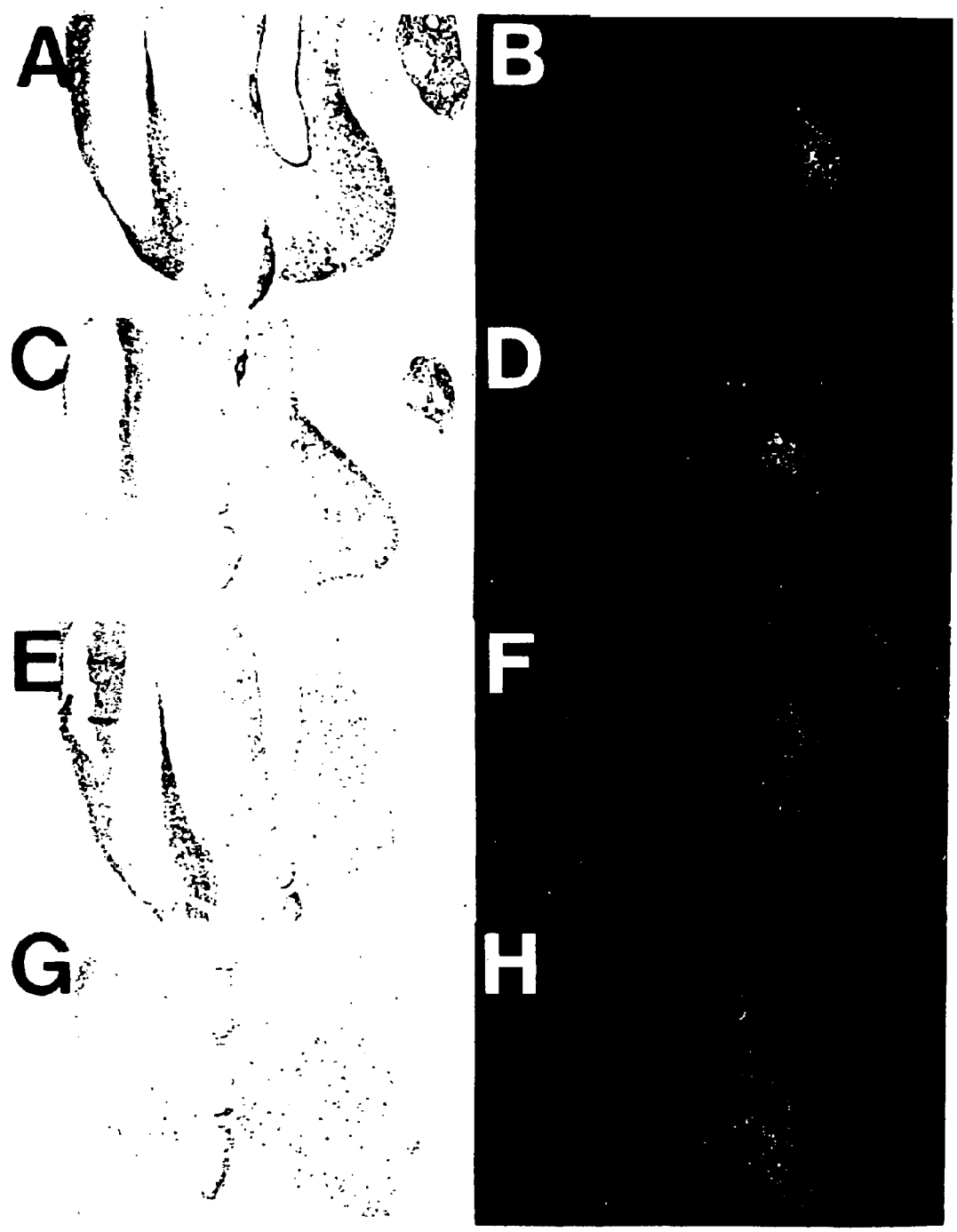
FIG. 1 is a microphotograph showing the expression of HGF mRNA in limb buds of mice at the early developmental stage (the left part is bright field, the right part is corresponding dark field).

As HGF used in the present invention, there can be used one which prepared by various methods if it is purified to an extent that it can be used as a medicine.

Various methods are known for preparing HGF. For example, HGF can be obtained by extraction and purification from organs (e.g. liver, spleen, lung, bone marrow, brain, kidney, placenta and the like), serum, plasma and blood cells (e.g. platelet, leucocyte and the like) of mammals such as rat, cow, horse, sheep and the like (see FEBS Letter, 224, 312, 1987; Proc. Natl. Acad. Sci. USA, 86, 5844, 1989, and the like).

Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises cloning the gene coding HGF with a proper vector, inserting it into a proper host cell to give a transformant, and separating the desired recombinant HGF from the culture supernatant of the transformant (e.g. Nature, 342, 440, 1989, Japanese Patent Kokai No. 111383/1993, Biochem. Biophys. Res. Commun., 163, 967, 1989). The host cell is not specifically limited, and various host cells conventionally used in gene engineering methods can be used, which are, for example, Escherichia coli, Bacillus subtilis, yeast, filamentous fungi, and plant or animal cells.

More specifically, the method of extracting and purifying HGF from live tissues is, for example, to administer carbon tetrachloride to a rat intraperitoneally, remove a liver from the rat with hepatitis, grind it, and purify by the ordinary protein purifying technique such as gel column chromatography using S-Sepharose and heparin Sepharose, HPLC and the like.

Further, by the gene engineering method, the gene coding the amino acid sequence of human HGF is cloned into a vector such as bovine papilloma virus DNA and the like to obtain an expression vector, and by using this expression vector, animals cells such as Chinese hamster ovary (CHO) cells, mouse C127 cells, monkey COS cells and the like are transformed, and HGF can be obtained from the culture supernatant of the transformants.

In thus obtained HGF, a part of the amino acid sequence of HGF may be deleted or substituted by other amino acid(s), another amino acid sequence may be inserted, one or more amino acids may be bonded to the N-terminal and/or C-terminal, or saccharide chain(s) may likewise be deleted or substituted, providing it has substantially the same effect as HGF.

The therapeutic agent and accelerator of the present invention comprise the above-mentioned HGF as an active component, and HGF promotes the proliferation of chondrocytes and has an effect to promote the production of proteoglycan, as shown in Test Examples mentioned later. Further, HGF has a feature that there is little tendency to cause side effect, since it shows no effect on the chondrocytes not injured and shows an effect only on the chondrocytes injured. Therefore, the therapeutic agent and accelerator of the present invention are effective for the treatment and prevention of various disorders caused by cartilaginous diseases, including, for example, the following disorders.

Osteoarthritis

Chondrodystrophy

Cure and restoration of fracture

Restoration of articular cartilage and articular disk due to injury

Acute suppurative arthritis

Tuberculous arthritis

Syphilitic arthritis

Rheumatoid arthritis

Rheumatic fever

Systemic lupus erythematosus

Spondylitis deformans

Herniated disk

Restoration due to bone transplantation

The therapeutic agent and accelerator of the present invention may be applied to the treatment and prevention of various disorders caused by cartilaginous diseases in human and the other animals (for example, cow, horse, pig, sheep, dog, cat and the like).

The therapeutic agent and accelerator of the present invention can be prepared in various preparation forms (e.g., liquid preparation, solid preparation, capsule preparation and the like), and in general, it is prepared in the form of injection preparation, inhalation preparation, suppository preparation or oral preparation containing HGF as the active component alone or together with common carrier. The afore-said injection preparation can be prepared by a conventional method, for example, it can be prepared by dissolving HGF in a suitable solvent (e.g., sterilized water, buffer solution, physiological saline and the like), sterilizing the solution by filtration through a filter or the like, and then filling the sterilized solution in aseptic vessels. The HGF content in the injection preparation may be usually from about 0.0002 to 0.2 (W/V %), preferably from about 0.001 to 0.1 (W/V %). Further, the oral preparation may be formed as a preparation such as a tablet, granule, grain, powder, soft or hard capsule, liquid preparation, emulsion, suspension, syrup and the like, and these preparations can be prepared by a conventional pharmaceutical method. The suppository preparation can also be prepared by a conventional pharmaceutical method using a common base (for example, cacao oil, laurin oil, glycero-gelatin, macrogol, witepsol and the like). Further, the inhalation preparation can be prepared by a conventional pharmaceutical method.

The HGF content in the preparation may be suitably adjusted depend on the preparation form, disease to be applied and the like.

In production of the preparation, a stabilizer is preferably added, and the stabilizer includes, for example, albumin, globulin, gelatin, glycine, mannitol, glucose, dextran, sorbitol, ethylene glycol and the like. Further, the preparation of the present invention may contain additives necessary for pharmaceutical preparation, for example, an excipient, a dissolving aid, an antioxidant, a pain-alleviating agent, an agent for isotonicity and the like. In the liquid preparation, it is preferable to store it under frozen conditions or after the removal of water by a process such as freeze-drying. The freeze-dried preparation is used by dissolving again in distilled water for injection and the like before use.

The therapeutic agent and accelerator of the present invention can be administered via a suitable administration route depend on the preparation form. For example, the injection preparation can be administered by intravenous, intraarterial, subcutaneous, intramuscular and the like. The dose is suitably adjusted depend on symptoms, age, body weight and the like of a patient, and usually from 0.05 mg to 500 mg, preferably from 1 mg to 100 mg of HGF is administered once or several times per day.

Industrial Applicability

In the present invention, an active component HGF has an effect to promote the proliferation of chondrocytes and to promote the production of proteoglycan. Therefore, the therapeutic agent and accelerator of the present invention are useful for the treatment and prevention of various disorders caused by cartilaginous diseases. Further, according to the invention, there can be obtained a medicine having little side effect, since HGF acts only on cartilaginous tissue injured.

EXAMPLE

The following Examples and Production Examples further illustrate the present invention in detail but are not to be construed to limit the scope thereof. The materials and methods used in the following experiments are shown below.

Materials and methods

① In situ hybridization

An EcoRI fragment (1.4 kb) of a rat HGF-cDNA (RBC1 clone) (Proc. Natl. Acad. Sci. USA, 87, 3200, 1990) was subcloned to a pGEM7 vector to produce sense and anti-sense RNA probes labeled with [a-$^{35}$S]UTP (400 Ci/mmol, manufactured by Amersham Ltd.). The labeled transcripts were hydrolyzed with an alkali to a 50 to 150 bases substance as a ribo-probe.

In situ hybridization was carried out by the method described in a literature (Biochem. Biophys. Res. Commun., 173, 42, 1990). The sample was fixed in 4% paraformaldehyde in phosphate-physiological saline solution, dehydrated with ethanol, washed with toluene, and then embedded in paraffin. 5 $\mu$m sections were cut and mounted on slide glasses coated with poly-L-lysine. The sections were deparaffinized with glycine and acetic anhydride, and hybridized with the probes at 50° C. for 16 hours. Then, the sections were washed with 0.1xSSC solution at 50° C. for 1 hour, treated with RNAase A (20 $\mu$g/ml) at 37° C. for 30 minutes, washed twice with 2xSSC solution at 37° C. for 10 minutes. The sections were immersed in an emulsion (1:1 dilution of Kodak NBT-2), and exposed to light for 2 weeks. The sections were developed with Kodak D-19, fixed and stained with hematoxylin-eosin.

② Cells and cell incubation

Chondrocytes were isolated from 23 day-old embryo and 4 week-old postnatal New Zealand white rabbit by the method described in a literature (J. Cell. Physiol., 133, 491, 1987). Articular cartilages were isolated from the knee joint femoral articular cartilage, and costal cartilages were isolated from the hyaline cartilage of rib (Dev. Biol., 136, 500, 1989). Synovial fibroblasts were isolated from the synovial tissue of knee joint. Minced fragments of the synovial tissue were cultured for 10 days in DMEM containing 10% FBS, and there were collected the proliferated cells by trypsin treatment. Embryonic mesenchymal cells were isolated from the limb muscular tissue of 20 day-old rat embryo by the method described in a literature (Exp. Cell Res., 157, 483, 1985). Limb bud mesenchymal cells were isolated from 10.5 day-old rat embryo. The limb buds were dissected under a surgical microscope, treated with 0.25% trypsin for 30 minutes, then pipetted and passed through a nylon sieve to isolate single cells. The all cells except limb bud cells were maintained in DMEM containing 10% FBS and 60 $\mu$g/ml kanamycin (hereinafter, referred to as medium A) at 37° C. under 5% $CO_2$/95% air.

③ Measurement of DNA synthesis

The DNA synthesis rate was evaluated by measuring the incorporation of [$^3$H]-thymidine ([6-$^3$]-thymidine, manufactured by Amersham Ltd., 20 Ci/mmol) into a 10% TCA insoluble-cell precipitate (J. Clin. Invest., 85, 626, 1990). The cells were seeded at a density of $1.5 \times 10^4/6$ mm well (96 wells plate), and incubated to be confluent. For the growth arrest, the cells were preincubated with 0.1 ml of DMEM containing 0.3% FBS. Various concentrations of HGF were added to the media. The incubation continued for 24 hours. One $\mu$Ci/ml of [$^3$H]-thymidine was added 3 hours before the termination of the incubation. After the labelling, the cells were washed three times with ice-cooled PBS, twice with 5% TCA containing 3 mM thymidine, once with ethanol/dimethyl ether (3:1). The residues in the well were solubilized with 100 $\mu$l of 0.1 N NaOH, transferred to a liquid scintillation vial, neutralized with 1 N HCl, and radioactivity was measured by a scintillation counter (Rack-beta, manufactured by Pharmacia Ltd.).

④ Measurement of proteoglycan synthesis

Chondrocytes were seeded at a density of $1.5 \times 10^4/6$ mm well, and maintained in 0.1 ml of the medium A. When the cells became confluent, they were preincubated for 24 hours in 0.1 ml of DMEM containing 0.3% FBS. Then, they were preincubated for 24 hours in 0.1 ml of DMEM containing 0.3% FBS and HGF. One $\mu$Ci/ml [$^{35}$S]-sulfate was added 20 hours before the termination of incubation. The proteoglycan synthesis was evaluated by measuring the incorporation of [$^{35}$S]-sulfate into a precipitate with cetylpyridinium chloride after protease digestion (Exp. Cell Res., 130, 73, 1980).

(5) Total RNA preparation and reverse transcribed PCR

Total RNA from cartilage was prepared by a modified method of the method described in a literature (Anal. Biochem., 203, 352, 1992). Freshly isolated tissue fragments (wet weight 0.1 g) were quickly homogenized in 2 ml of a 4 M GITC solution of 1% 2-mercaptoethanol, 0.1 M Tris-HCl (pH 7.5) and 4 M guanidine thiocyanate. The homogenate was mixed with 100 µl of 10% SDS, and the mixture was centrifuged by a microcentrifuge for 5 minutes. The supernatant (2 ml) was layed on the same volume of 1.6 g cesium trifluoroacetate and 1 mM EDTA (pH 8.0) in a Beckmann polyalloma centrifuge tube (13×51 mm). The samples were centrifuged at 35,000 rpm (147,000xg) for 20 hours at 18° C. The supernatant was removed under suction, then the precipitate was dissolved in 200 µl of 4 M GITC solution and extracted with phenol: chloroform: isoamyl alcohol (25:24:1), then the extracted material was mixed with 20 µl of 3 M sodium acetate (pH 4.8), and precipitated with 2-fold volume (440 µl) of ethanol. The precipitate was dissolved in DEPC-treated water.

First, a first-strand cDNA was synthesized from 0.5 µg of the total RNA using a SuperScript reverse transcriptase (Gibco-BRL) and downstream anti-sense primers. Subsequently, PCR amplification was carried out. The amplification was conducted in 35 cycles (in the case of chondrocytes) or 40 cycles (in the case of cartilaginous tissues), each cycle being conducted 30 seconds at 94° C., 1 minute at 59° C. and 1.5 minutes at 72° C. As a primer base sequence for PCR amplication a 725 bp fragment was prepared with 5'-CAGT(A/G)ATGATCTCAATGGGCAAT-3'(SEQ ID NO:1) and 5'AATGCCCTCTTCCTATGACTTC-3'(SEQ ID NO:2) for c-Met of a rat and mouse (Oncogene, 2, 593, 1988).

Example 1

HGF mRNA expression in developmental limb

The expression of HGF mRNA in the limb bud of a developmental mouse was tested by in situ hybridization method. The results are shown in FIG. 1, FIG. 2 and FIG. 3.

FIG. 1 shows the expression of HGF mRNA in limb buds of early developmental stage mice, and is a microphotograph of longitudinal sections of the hind-limb. The bright field (left part) and the corresponding dark field (right part) were photographed after in situ hybridization, autoradiography and staining. In this figure, each A to D indicates the section of a 0.5 days p.c. embryo, and each E to H indicates the section of a 11 days p.c. embryo.

Figure 2:
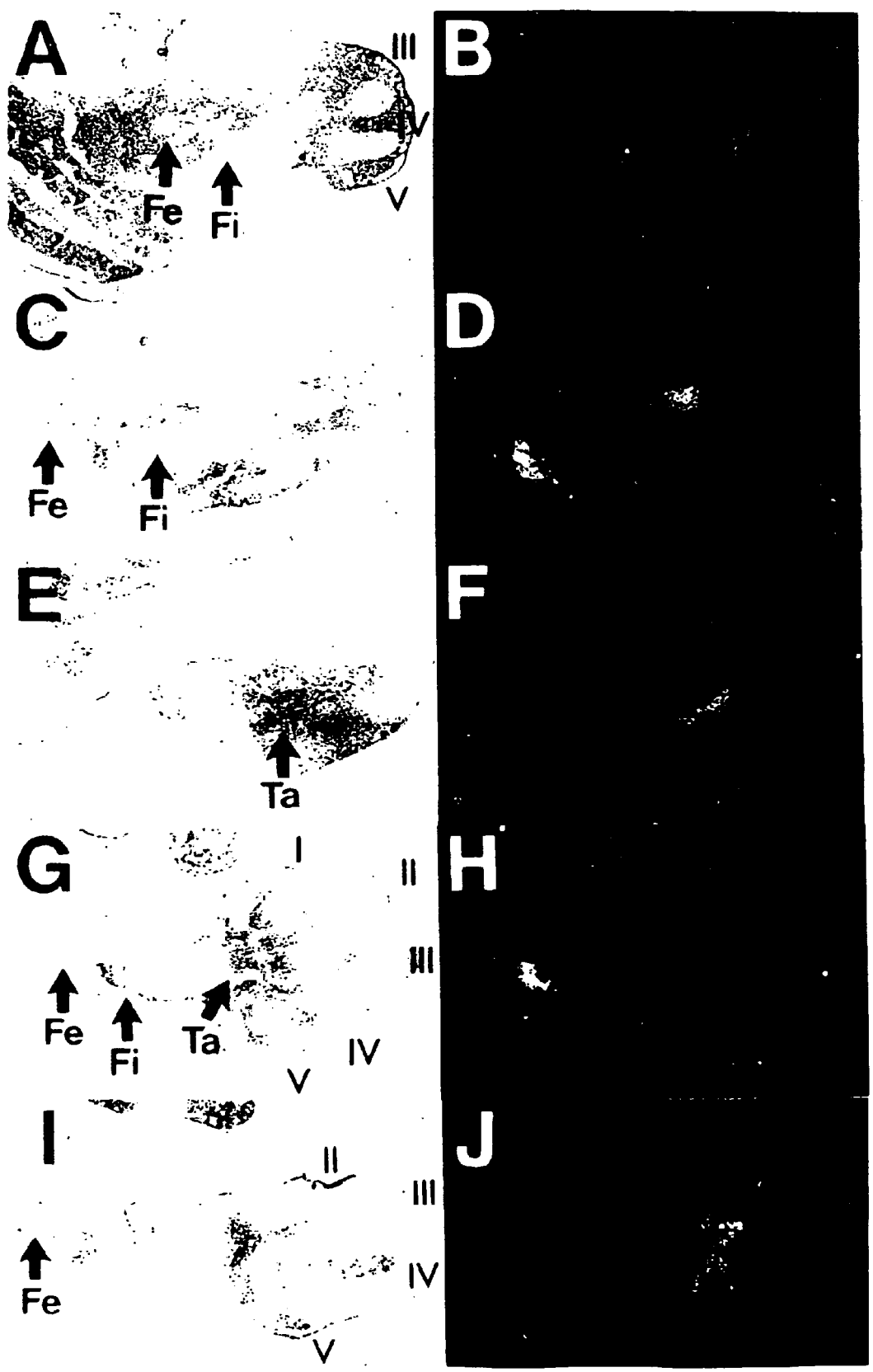
FIG. 2 is a microphotograph showing the expression of HGF mRNA in limb buds of mice at the digitus forming stage (the left part is bright field, the right part is corresponding dark field).

FIG. 2 shows the expression of HGF mRNA in limb buds of digitus forming stage mice, and is a microphotograph of longitudinal sections of the hind-limb. The bright field (left part) and the corresponding dark field (right part) were photographed after in situ hybridization, autoradiography and staining. In this figure, each A and B indicates the section of a 12.5 days p.c. embryo, each C to F indicates the section of a 13 days p.c. embryo, and each G to J indicates the section of a 14 days p.c. embryo. Further, Fe indicates a femur, Fi indicates a fibula, Ta indicates a tarsal bone, and each I to V indicates digit number.

Figure 3:
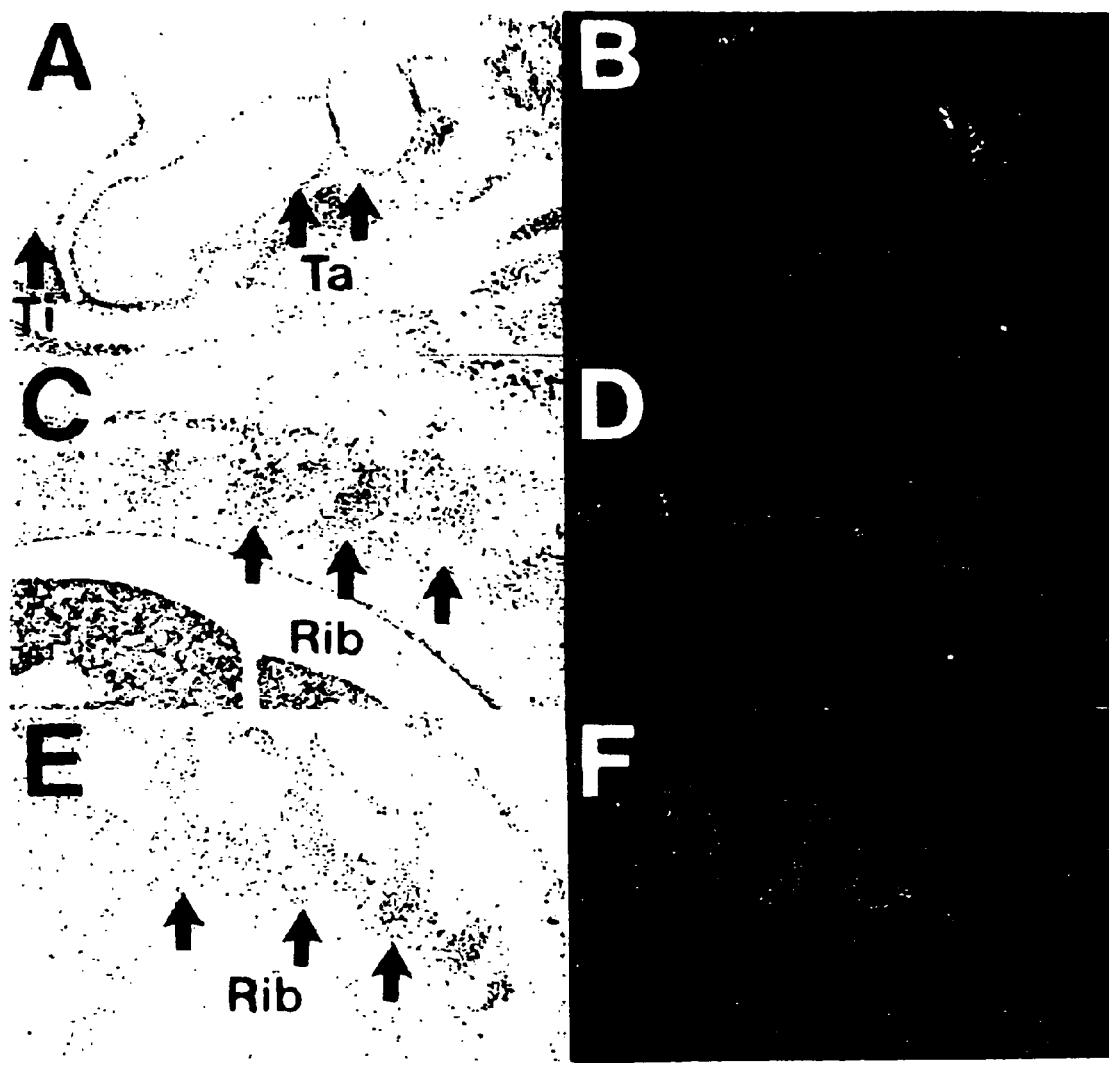
FIG. 3 is a microphotograph showing the expression of HGF mRNA in limb buds and thoraxes of mice at the developmental stage (the left part is bright field, the right part is corresponding dark field).

FIG. 3 is a microphotograph showing the expression of HGF mRNA in limb buds and thoraxes of mice at developmental stage, and the bright field (left part) and the corresponding dark field (right part) were photographed after in situ hybridization, autoradiography and staining. In this figure, each A and B indicates the horizontal section of the hind limb of a 16 days p.c. embryo, each C and D indicates the longitudinal section of the thorax of a 13 days p.c. embryo, each E and F is the longitudinal section of the thorax of a 14 days p.c. embryo. Further, Ta indicates a tarsal bone, Ti indicates a tibia and Rib indicates the precartilaginous condensation of rib cartilage.

As shown in FIG. 1, there was detected the diffuse expression of HGF mRNA around the bottom region of the limb on 11th day. At this stage, the cartilaginous condensation was not formed in the limb. With the progress of the cartilaginous condensation, the expression site of HGF mRNA became more restricted. When stylopodium, zygopodium and autopodium were formed on 12.5th day, the expression of HGF mRNA was observed at wrist/heel and elbow/knee joint regions (see FIG. 2A and B). For convenience, knee and heel are shown). In the later stage (13 to 14 days), HGF MRNA was expressed in the restricted mesenchymal cells adjacent to the cartilaginous condensation at wrist/heel and elbow/knee joint regions (see FIG. 2C to J). On 16th day, HGF mRNA was localized in the restricted mesenchymal cells adjacent to the cartilage of tarsal bone (see FIG. 3A and B). The expression level in the limb of HGF mRNA was decreased with the differentiation. Throughout the tests, HGF mRNA was not detected in the growing disk of hand and foot.

Example 2

HGF mRNA expression in developing thorax

The expression of HGF mRNA in the thorax of developing mouse was tested by in situ hybridization method. The results are shown in FIG. 3C to F.

As shown in FIGS. 3C to F, HGF mRNA was expressed in an ambient intercostal mesenchymal tissue at the end point of a precartilaginous condensation formed by extension of the intercostal bone. In the precartilaginous condensation, the signal of hybridization was not detected.

Example 3

Scatter activity test of HGF on chondrocytes

To determine which is the target cell of HGF around the differentiating cartilage tissue, there were prepared the cultured cells of chondrocytes derived from articular cartilage of knee joint and costal cartilage, synovial cells derived from knee joint and fibroblasts proliferated from limb muscular tissue, and the effects of HGF exogenously added to these cells were examined.

Namely, articular chondrocytes of rabbit were seeded at a density of 3×10³/16 mm well, and maintained in medium A for 2 days. Then, the chondrocytes were treated with HGF for 2 days. When the incubation was over, phase-contrast photomicrographs were taken. The results are shown in FIG. 4.

Figure 4A:
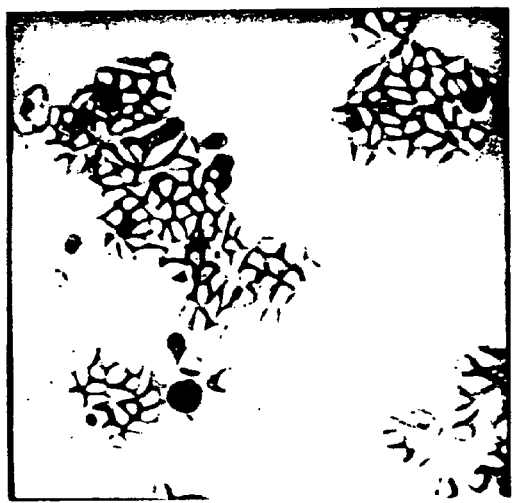
FIG. 4 is a microphotograph showing the scatter activity of HGF on chondrocytes.
Figure 4B:
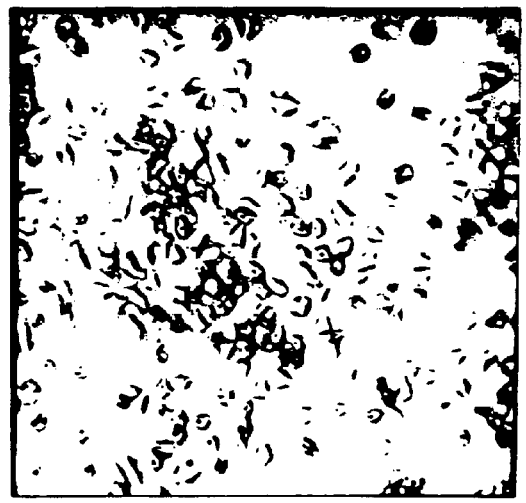

As shown in FIG. 4, in no-HGF-treated test (control), polyhedron chondrocytes proliferated and formed islands (FIG. 4A). On the other hand, in the culture treated with HGF (3 ng/ml), each chondrocytes existed a single cell and did not form an island (FIG. 4B). Therefore, it became clear that HGF stimulates the migration of chondrocytes. In contrast, HGF scattered neither fibroblasts nor synovial cells.

Example 4

Effect of HGF on chondrocyte proliferation

The effect of HGF on chondrocytes proliferation was examined.

Namely, articular chondrocytes isolated from 4 week-old rabbit were incubated. The cells which had become confluent was subjected to serum deleting treatment for 24 hours, then treated with various concentrations of HGF, and the incorporation amount of [$^3$H]-thymidine was measured by the method described in the aforesaid Materials and Methods. Further, the same test was conducted with respect to the rabbit synovial fibroblasts. The results are shown in FIGS. 5A (articular chondrocytes) and 5B (synovial fibroblasts). Here, the result is shown in terms of average ± standard deviation of three tests (likewise also in FIG. 5C, FIG. 6 and FIGS. 7A and B).

As shown in FIG. 5A, HGF increased the incorporation of [$^3$H]-thymidine into rabbit articular chondrocytes depending on the dose, and had an effect to promote DNA synthesis, namely an effect to promote proliferation of the articular chondrocytes. With 1 ng/ml HGF, DNA synthesis was recognized to increase three times against the control. On the other hand, as shown in FIG. 5B, the synovial fibroblasts did not react to HGF.

Further, in the other experiment, the effect of HGF on the cell number of articular cartilage was examined. Namely, rabbit articular chondrocytes were seeded at a density of 1×10$^4$/16 mm well, and maintained in a DMEM medium containing 10% FBS. Then, 10 ng/ml HGF was added and the mixture was incubated for 48 hours, and after the incubation, the cell number was measured. The results were shown in FIG. 5C.

As shown in FIG. 5C, 10 ng/ml HGF increased the cell number 1.8 times as compared with the control.

Example 5
Effect of HGF on proteoglycan production

Figure 6:
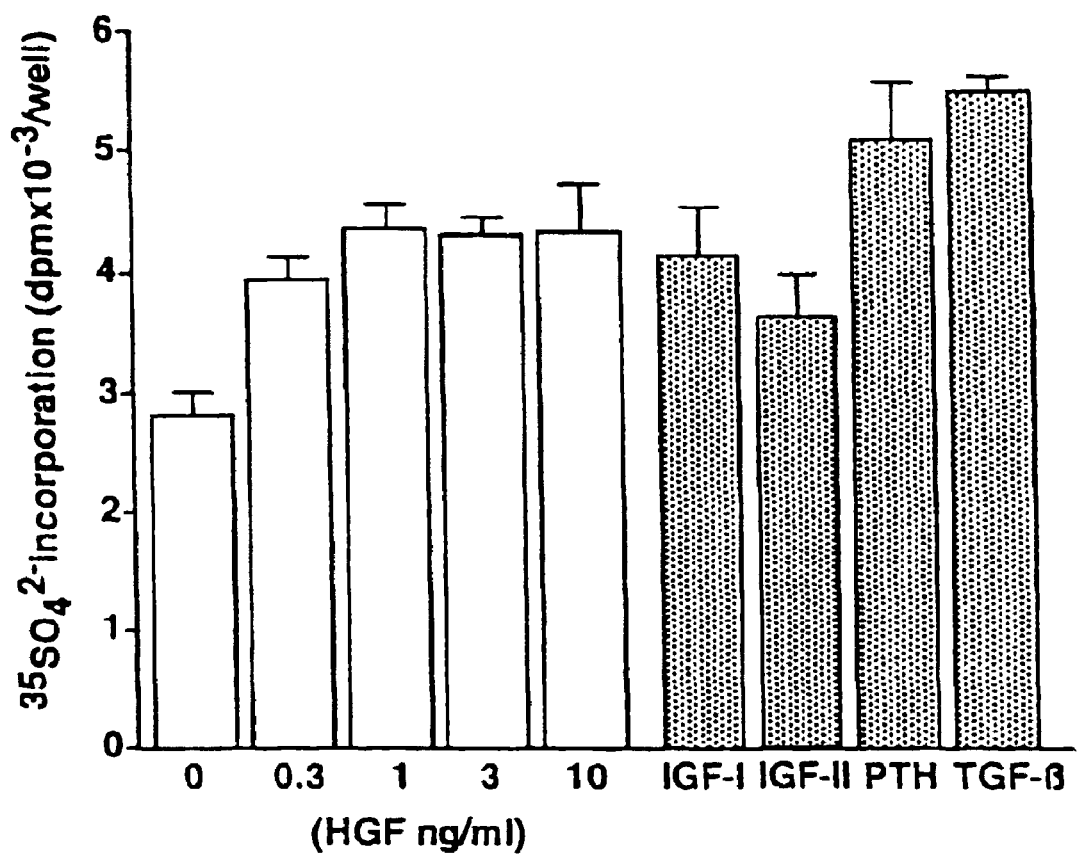
FIG. 6 is a drawing showing the effect of HGF on proteoglycan production.

Since HGF promoted the proliferation of chondrocytes as described above, the effect of articular chondrocytes on proteoglycan production was examines by the method described in the aforesaid Materials and Methods. The proteoglycan synthesis was evaluated by measuring the incorporation of [$^{35}$S]-sulfate into macromolecules (glycosaminoglycans) precipitated with cetylpyridinium chloride after protease digestion (Exp. Cell Res., 130, 73, 1980). Further, there were conducted tests on the following factors instead of HGF. Insulin-like growth factor (IGF)-I: concentration 100 ng/ml IGF-II: concentration 100 ng/ml Parathyroid hormone (PTH): concentration 10$^{-7}$ M TGF-β: concentration 3 ng/ml The results are shown in FIG. 6. As shown in FIG. 6, HGF increased the incorporation of [$^{35}$S]-sulfate depending on the dose. The maximum increase was recognized at 1 ng/ml HGF. This effect is approximately the same as those of IGF-I and II (Exp. Cell Res., 130, 73, 1980), though weaker than those of TGF-β (J. Cell Physiol., 138, 329, 1989) and PTH (J. Clin. Invest., 85, 626, 1990).

Example 6
Effect of HGF on DNA synthesis and proteoglycan production in the presence of anti-HGF antibody As described above, HGF is usually thought to act on target cells by paracrine mechanism, and it is considered that the result of the aforesaid in situ hybridization supports this idea. Then, to recognize this point, it was examined whether or not the anti-HGF polyclonal antibody modulates the functions of chondrocytes.

Namely, rabbit articular chondrocytes which had become confluent were treated with 25 μg/ml anti-HGF polyclonal antibody (IgG fraction purified by affinity) or not treated in the presence or absence of 3 ng/ml HGF. Then, the chondrocytes were labeled with [$^3$H]-thymidine or [$^{35}$S]-sulfate by the method described in the aforesaid Materials and Methods to measure the DNA synthesis or proteoglycan production. The results are shown in FIG. 7A (DNA synthesis) and B (proteoglycan production). In these figures, Ab indicates an anti-HGF polyclonal antibody.

As shown in FIG. 7, the addition of the anti-HGF polyclonal antibody alone did not change the DNA synthesis and proteoglycan production in the articular chondrocytes. However, the anti-HGF polyclonal antibody completely blocked the effect of the exogenously added HGF. This means that chondrocytes do not produce sufficient HGF to modulate the functions of themselves.

Example 7

Expression of HGF receptor mRNA in chondrocytes

The expression of HGF receptor (c-Met) in chondrocytes in vivo and in vitro was examined by reverse transcription PCR. Various parts of articular tissue and costal cartilage were dissected out from 4 week-old rat under a surgical microscope, and the total RNA was extracted as described in Materials and Methods. The extracted RNA (0.5 μg) was subjected to reverse transcription, amplified using c-Met primers, and then analyzed by 1.5% agarose gel electrophoresis. The results are shown in FIG. 8.

Figure 8:
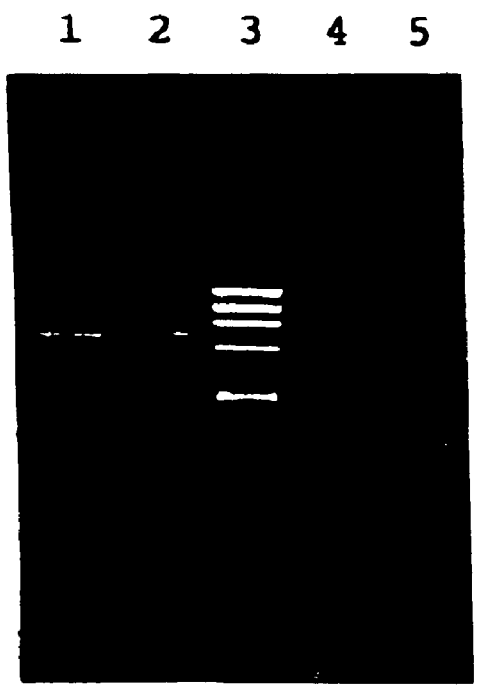
FIG. 8 is an electrophoretic photo showing the expression of HGF receptor mRNA in chondrocytes.

As shown in FIG. 8, after the amplification was repeated 40 cycles with respect to the articular chondrocytes and costal chondrocytes, slight c-Met expression was detected, and after the amplification of the cultured chondrocytes was repeated 35 cycles, remarkable c-Met expression was detected.

Production Example 1

| Production example of HGF preparation | | |
|---|---|---|
| (1) | HGF | 20 μg |
| | human serum albumin | 100 mg |

The above-mentioned substances were dissolved in 0.01 M PBS of pH 7.0, and the total amount was adjusted to 20 ml and sterilized. The solution was poured into vials by 2 ml, freeze-dried and sealed.

| (2) | HGF | 40 μg |
|---|---|---|
| | Tween 80 | 1 mg |
| | human serum albumin | 100 mg |

The above-mentioned substances were dissolved in physiological saline for injection, and the total amount was adjusted to 20 ml and sterilized. The solution was poured into vials by 2 ml, freeze-dried and sealed.

What is claimed is:

1. A method of treating cartilaginous diseases and disorders in mammals comprising administering a wild-type full length Hepatocyte Growth Factor (HGF) in an amount which is effective in treating said cartilaginous diseases and disorders, wherein said cartilaginous diseases and disorders are osteoarthritis, chondrodystrophy, failure in restoration and cure of fracture, articular cartilage and articular disk injury, acute suppurative arthritis, tuberculous arthritis, syphilitic arthritis, rheumatoid arthritis, rheumatic fever, systemic lupus erythematosus, spondylitis deformans, or herniated disk.

2. The treatment method for cartilaginous diseases and disorders according to claim 1, wherein the HGF is prepared by gene recombination.

3. The method of treating cartilaginous diseases and disorders in mammals according to claim 1, wherein said cartilaginous disease is osteoarthritis.

4. The method of treating cartilaginous diseases and disorders in mammals according to claim 1, wherein said cartilaginous disease is chondrodystrophy.

5. The method of treating cartilaginous diseases and disorders in mammals according to claim 1, wherein said cartilaginous disorder is failure in restoration and cure of fracture.

6. The method of treating cartilaginous diseases and disorders in mammals according to claim 1, wherein said cartilaginous disease is articular cartilage and articular disk injury.

7. The method of treating cartilaginous diseases and disorders in mammals according to claim 1, wherein said cartilaginous disease is acute suppurative arthritis.

8. The method of treating cartilaginous diseases and disorders in mammals according to claim 1, wherein said cartilaginous disease is tuberculous arthritis.

9. The method of treating cartilaginous diseases and disorders in mammals according to claim 1, wherein said cartilaginous disease is syphilitic arthritis.

10. The method of treating cartilaginous diseases and disorders in mammals according to claim 1, wherein said cartilaginous disease is rheumatoid arthritis.

11. The method of treating cartilaginous diseases and disorders in mammals according to claim 1, wherein said cartilaginous disease is rheumatic fever.

12. The method of treating cartilaginous diseases and disorders in mammals according to claim 1, wherein said cartilaginous disease is systemic lupus erythematosus.

13. The method of treating cartilaginous diseases and disorders in mammals according to claim 1, wherein said cartilaginous disease is spondylitis deformans.

14. The method of treating cartilaginous diseases and disorders in mammals according to claim 1, wherein said cartilaginous disorder is herniated disk.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer directed to c-Met of a rat and mouse.

<400> SEQUENCE: 1
cagtratgat ctcaatgggc aat                                           23

<210> SEQ ID NO 2
<211> LENGTH: 22
<212> TYPE: DNA
<213> ORGANISM: Artificial Sequence
<220> FEATURE:
<223> OTHER INFORMATION: Primer directed to c-Met of a rat and mouse.

<400> SEQUENCE: 2
aatgccctct tcctatgact tc                                            22